Figure 1:
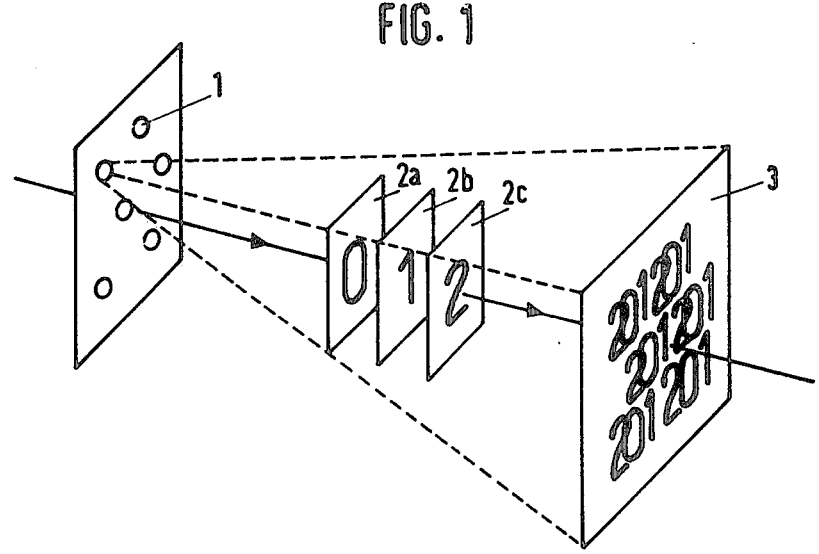

United States Patent [19]

Geluk

[11] 4,191,890
[45] Mar. 4, 1980

[54] SYNTHETIC APERTURE SCANNER FOR DECODING A CODED IMAGE PRODUCED BY PENETRATING RADIATION, SUCH AS X-RAYS

[75] Inventor: Ronald J. Geluk, Nootdorp, Netherlands

[73] Assignee: N.V. Optische Industrie "De Oude Delft", Delft, Netherlands

[21] Appl. No.: 854,701

[22] Filed: Nov. 25, 1977

[30] Foreign Application Priority Data

Dec. 3, 1976 [NL] Netherlands ......................... 7613502

[51] Int. Cl.$^2$ ............................................. G03B 41/16
[52] U.S. Cl. .............................. 250/402; 250/416 TV; 250/514; 358/111
[58] Field of Search ................. 250/401, 402, 416 TV, 250/505, 514; 358/111

[56] References Cited

U.S. PATENT DOCUMENTS

| | | | |
|---|---|---|---|
| 3,831,031 | 8/1974 | Barrett | 250/320 |
| 3,882,310 | 5/1975 | Barrett | 250/492 R |
| 4,023,037 | 5/1977 | Weiss | 250/323 |
| 4,087,837 | 5/1978 | Geluk | 250/510 |

Primary Examiner—Craig E. Church
Attorney, Agent, or Firm—O'Brien & Marks

[57] ABSTRACT

A system for decoding a coded aperture image of an object exposed to short-wave radiation from a plurality of point sources positioned in space in accordance with a given distribution. The coded aperture image is displayed by a cathode ray tube having its screen optically coupled to the entrance screen of an image intensifier tube. This image intensifier tube is effective to consecutively shift its entrance screen image in its entirety along a field pattern of lines. The images thus produced on the exit screen of the intensifier tube are transferred through a mask system having a transparency pattern related to the distribution pattern of said point sources, to a detector which position wise integrates the light transmitted through said mask system.

8 Claims, 2 Drawing Figures

SYNTHETIC APERTURE SCANNER FOR DECODING A CODED IMAGE PRODUCED BY PENETRATING RADIATION, SUCH AS X-RAYS

This invention relates to apparatus for decoding a coded image formed by penetrating radiation, such as X-rays, projected from a plurality of sources of radiation, being substantially point sources, arranged in a given spatial distribution pattern.

It is known, for example, from an article by G. Groh, entitled "Neue Wege Darstellung 3-dimensionaler Röntgenbilder" (New ways of producing X-ray images), in order to obtain an X-ray image that is free from blurring as a result of relatively rapid movements of the object being viewed, to use a plurality of X-ray sources arranged in a quasi-random spatial distribution pattern, which sources are simultaneously excited to issue a burst of radiation. From an object thus irradiated with bursts of radiation there is produced a coded X-ray image containing information from a plurality of layers of the object or "object slices", in such a manner that the information associated with a given object slice is superimposed on that associated with a different object slice, and that the images produced by each of the X-ray sources are recorded in superimposed relationship. In order for such an image containing superimposed information, referred to herein as a coded image, to be decoded, use must be made of a key configuration corresponding to the quasi-random distribution pattern according to which the X-ray sources are arranged in space.

The above article proposes performing the decoding operation electronically, using a disk memory in which the image to be decoded is stored in the first place. The stored image can then be written into a so-called scan converter, or an apparatus in which a light image can be converted into a charge image, which can be read in a non-destructive manner. By means of such a converter, images can be added electronically. In this known organization, each image associated with an X-ray source is separately positioned and stored in accordance with the position of the X-ray source in the distribution pattern. Accordingly, with a pattern of n apertures, corresponding with n X-ray sources, each image is positioned, entered and stored n times, under the control of a computer, to produce an image that is the decoded version of an object slice as determined by the pattern imaging parameters.

This prior technique has the drawback that, on the one hand, the structural organization involves a complicated and relatively expensive system, and on the other hand, the machine time required for the performance of the decoding operation is relatively long. In this connection it should be noted that the quality or definition of the ultimate image obtained after decoding is better as a larger number of x-ray sources are used. This means that the machine time required will likewise be increased if one wants to improve image quality in this manner. If, for example, a single sub-series comprising the positioning of the aperture pattern and the entry and storage of image data requires a machine time interval of approx. 50 milliseconds, a source configuration comprising 10 radiation sources will require a machine time interval as long as at least 500 milliseconds for the decoding of a single object slice.

It is an object of the present invention to eliminate these drawbacks, and to provide a decoding apparatus capable of carrying out a decoding operation in a considerably shorter period of time, which moreover is not increased when a larger number of radiation sources is used.

According to the present invention, there is provided apparatus for decoding a coded image formed by penetrating radiation, such as X-rays, projected from a plurality of sources of radiation, being substantially point sources and arranged in a given spatial distribution pattern, and comprising means for spatially shifting a thus coded image in accordance with the distribution pattern of the radiation sources; integrating means for integrating the image signals obtained from such shifting step; and reproduction means for bringing an electrical signal formed by said integrating means into a form suitable for presentation; characterized by an image intensifier with an output screen having a short persistence and associated deflector means for bodily shifting an electron-optical image formed in the image intensifier according to a frame of image lines; converter means for forming an image derived from the radiation image to be decoded on the input screen of said image intensifier; one or more masks, each having a pattern corresponding to the distribution pattern of the sources of radiation, and optically coupled to the output image of said image intensifier; and an image detector disposed behind each mask for integrating all of the light passed by said mask according to position.

Apparatus arranged in accordance with the present invention makes it possible for the decoding operation on a presented coded image of an object to be carried out so fast that a decoded image of a selected object slice can be presented virtually immediately (i.e. within a time interval that is negligible to the user) after the formation of a coded image of the object caused by a burst of radiation. In other words, operation on the basis of real time is possible. For example, a decoded image of a given object slice can be presented at a rate of 50 images per second. In principle, therefore, the present invention provides the possibility of producing motion pictures.

According to a preferred feature of the present invention, said converter means for forming an electron-optical image derived from the radiation image to be decoded on the input screen of the image intensifier comprises a lens system with an adjustable magnification factor. This makes it possible for the user to select a given slice of the object by selection of the magnification factor. In principle, such an adjustable magnification factor can also be incorporated in a lens system disposed opposite the output screen of the image intensifier. The essential point here is just the ratio between the size of the distribution pattern of the sources and the size of the image formed on the input screen of the image intensifier and the size of the image projected on said mask.

One embodiment of the present invention, with some variants, will now be described, by way of example, with reference to the accompanying drawings. In said drawings, FIG. 1 illustrates diagrammatically the formation of a coded image of a 3-dimensional object, using a plurality of point sources; and FIG. 2 is a diagram of one embodiment of apparatus according to the present invention for decoding the coded image.

Referring now to the drawings, FIG. 1 illustrates diagrammatically the way in which, starting from a plurality of point sources of radiation, e.g. X-ray sources, such as 1, arranged in space according to a given function, a coded radiation image is formed from a 3-dimensional object 2, in particular object slices 2a, 2b and 2c, on a screen 3, when, for example, the sources of radiation are simultaneously pulse-excited to irradiate the object with a brust of radiation from these sources. The coded radiation image formed on screen 3 is in principle a superposition of the partial images formed by each of the sources of radiation, each such a partial image being in turn a superposition of the information present in the slices of the object being viewed. It is an object of the present invention to provide apparatus for decoding such a coded image by simple means and in a fast manner, so that an image corresponding to a selected object slice can be presented on the basis of real time. The quality of such a decoded image is improved as the number of radiation sources used is increased with the spatial distribution thereof being a so-called non-redundant distribution, i.e. when such a pattern is scanned with an identical pattern, there is only one position in which all the image fragments projected by the n radiation sources coincide, and in other positions not more than a few coincidences occur.

Figure 2:
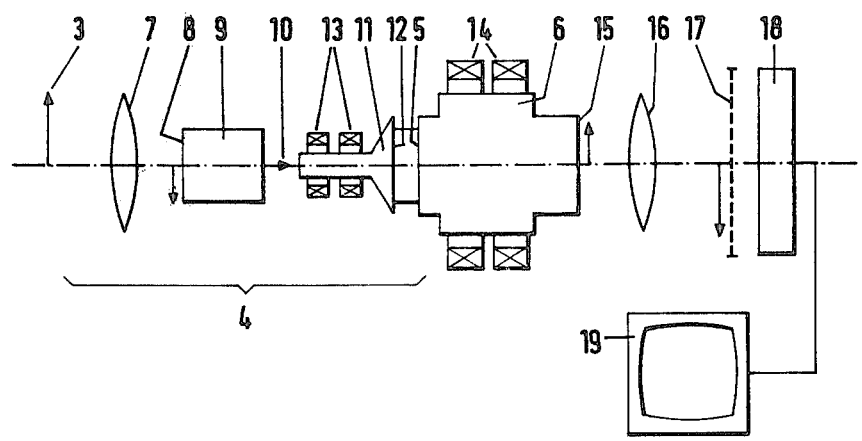

FIG. 2 is a diagram of an embodiment of apparatus according to the present invention, by means of which a coded image, processed as described in conjunction with FIG. 1 can be decoded. In it, use is made of a system organization closely related to that of a so-called synthetic aperture scanner as proposed in U.S. Pat. No. 4,097,898.

The embodiment of decoding apparatus according to the present invention as illustrated in FIG. 2 comprises converter means generally indicated at 4, and serving to form an electron-optical image, derived from a radiation image to be decoded, as processed, for example, as described in conjunction with FIG. 1, on the input screen 5 of an image intensifier 6. The converter means comprise a lens system 7 arranged to depict the image to be decoded on the input screen 8 of an image converter 9, if desired with a selectable magnification factor, the image converter being capable of forming on the output 10 an electrical signal corresponding to an image presented to it. Output 10 is connected to the luminance modulation input of a cathode ray tube 11 with a persistant screen 12. Screen 12 is optically coupled to the input screen 5 of image intensifier 6. When, during the presentation of the coded image to the image converter 9, the deflector means associated with the cathode ray tube 11 are controlled, in a manner known per se, so that the electron beam sweeps a frame of image lines, the coded image can be written on the screen 12. The image thus written on screen 12, which owing to the persistency of the screen is retained for a suitable period of time, is presented to the input screen 5 of image intensifier 6. By a known per se technique the deflector means 14 associated with image intensifier 6 can be caused to effect, generally magnetically, that the image formed on the inut screen 5 is bodily shifted according to a frame of lines of a form conventional in the video art. It can thus be achieved that the image formed on screen 15 can be bodily shifted to and fro across the video frame, with the understanding that the image as a whole is shifted by one line in, for example 64 microseconds, and traverses a whole frame in 20 milliseconds.

The image thus rapidly shifted to and fro on the output screen 15 of the image intensifier is depicted by means of a lens system 16 on a mask 17 with a pattern of apertures corresponding to the spatial distribution of the radiation sources used for forming the coded image. If desired, the magnification factor at which the image formed on screen 15 is depicted on mask 17 by this lens system can be made adjustable to provide a possibility of adjustment for selecting the object section ultimately to be depicted in decoded form. Such a possibility of adjustment is also given by the variation of the magnification factor as determined by lens system 7, with which the ratio between the size of the presented coded image and the size of the image as formed on the screen 12 of the cathode ray tube can be adjusted.

In principle, the pattern of apertures formed in mask 17 will have to be representative of the actual deconvolution function of the spatial arrangement of the radiation sources. A pattern of apertures corresponding to the spatial distribution of the radiation sources is in fact an approximation of ideal image decoding. For the so-called point-spread function of the system taken as a whole is then the autocorrelation function of the distribution of the sources. Image quality can be improved in this respect by an increase of the number of sources used for irradiating the object.

If, for practical reasons, a small number of sources are used, a preferred pattern is one corresponding to the deconvolution function of the source distribution; such a pattern, however, is considerably more complex than the above approximation. Starting, for example, from 10 radiation sources, the deconvolution of the distribution of these sources is, by the first approximation, the distribution pattern of these sources, in other words, a pattern of 10 apertures. By the second approximation, the deconvolution is given by the same pattern less the undesirable part of the autocorrelation function convoluted with the source distribution (10.90...), and by the next approximation less the undesirable part of the previous function convoluted with the source distribution (10.900...); etc. This illustration will show that, using the principles of the prior art, as described hereinbefore, the machine time required for the performance of a decoding operation becomes increasingly longer as one seeks to improve the quality of the decoded image.

With a synthetic aperture scanning apparatus, however, as used for the purposes of the present invention, it is just a matter of mask selection that determines ultimate image quality. The image is always available within an imaging period, i.e., the time needed to write a complete image into the cathode ray tube.

In the arrangement of FIG. 2, an image or light detector 18 is provided posterior to mask 17. This detector simultaneously collects all the light passed by the apertures of the mask, the light passed being integrated according to position. The light detector is formed, for example, as a photomultiplier, at the output of which a video signal is obtained, which is representative of a decoded object slice. This video signal is supplied to a reproducing apparatus 19 capable of presenting this video signal in a suitable form. Thus, for example, it is possible for the image formed on the reproduction apparatus, formed as a monitor, to be presented at a frequency of 50 images per second.

With a decoding system of the arrangement described, a decoded image is available extremely rapidly, namely, always at one imaging period, which also provides the possibility of obtaining a sectional image of moving objects.

As stated before, a sharp picture of a given object slice can be obtained through selection of the magnification factor applied, either that between the coded image presented and the input screen of the image intensifier, or that between the output screen of this image intensifier and the mask referred to. Naturally, the magnification factor can be adjusted by electronic means, which also makes it possible for such an adjustment to be effected by means of the image intensifier. Such an electronic control of the magnification factor can, for example, be programmed so that, for example, a different object slice is presented every 20 milliseconds, i.e., the time interval in which an image presented is shifted by a complete frame. Accordingly, a control of the magnification factor is not restricted to a control of the optical system, such as a zoom lens. Electronic control of the magnification factor offers the possibility of moving through the object slices at a relatively high velocity.

For the sake of completeness it is noted that it is naturally possible, within the scope of the present invention, to use a mask transmission function with negative parts in a manner similar to that described in the above prior U.S. Pat. No. 4,097,898. This is of importance if the deconvolution function referred to is used, which may assume negative values.

Within the framework of the present invention it is also possible, instead of a two-dimensional pattern of radiation sources (X-ray sources), to use a one-dimensional pattern of radiation sources arranged according to a free, quasi-random distribution. In other words, when an object is irradiated with sources thus distributed, the image area is limited to an object slice, i.e., a section on the line along which the sources of radiation are arranged. With such an organization, and using a decoding system arranged in accordance with the present invention, a sharp picture of an object line can be obtained. Continuous control of the magnification factor between the decoding filter and the coded image makes it possible for these lines of sharpness to be shifted, which comes down to the reconstruction of an object slice. The magnification factor is here given as the size of the source pattern with which the lines of sharpness are subsequently scanned. The deconvolution function being one-dimensional in this case, a continuous series of functions can be incorporated in a mask. The magnification factor can then be obtained by electronic control means performing a translation of the output image of the image intensifier instead of the magnification factor control arrangements described hereinbefore.

In an alternative embodiment of this organization in which a plurality of radiation sources are arranged in a one-dimensional pattern with quasi-random distribution, a single source may be rapidly moved by transport mans along such a track, during which movement the source is switched by switching means according to an on-off function corresponding to the quasi-random distribution according to which the sources are arranged in the previous example.

It is also possible, in the above two alternative embodiments, to shift the detector surface in a plane perpendicular to the plane determined by the radiation during the irradiation of the object, which provides a recording distributed over a surface, whereby distorting intermodulation effects in the image reproduction are prevented.

It is also possible for the radiation source to be moved along a non-straight line parallel to the detector surface, which naturally should be taken into account during the subsequent decoding step. For in that case the deconvolution function is different for each point to be decoded. The system according to the present invention functions so fast as to allow the practical implementation of a system based on this principle. For example, such a non-straight line along which the source is moved may be a circle.

I claim:

1. Apparatus for decoding a coded image formed by penetrating radiation, such as X-rays, projected from a plurality of sources of radiation which sources are substantially point sources and arranged in a given spatial distribution pattern, the apparatus comprising means for spatially shifting a thus coded image in accordance with the distribution pattern of the radiation sources; integrating means for integrating and generating an electrical signal from the coded image obtained from such shifting means; reproduction means for bringing the electrical signal formed by said integrating and generating means into a form suitable for presentation, said shifting means including an image intensifier with an output screen having a short persistence and associated deflector means for bodily shifting an electron-optical image formed in the image intensifier according to a frame of image lines, and converter means for forming an image derived from the radiation image to be decoded on the input screen of said image intensifier; said integrating and generating means including one or more masks, each having a pattern corresponding to the distribution pattern of the sources of radiation and optically coupled to the output image of said image intensifier, and an image detector disposed behind each mask for integrating all of the image passed by said mask.

2. Apparatus according to claim 1, wherein the optical coupling between the output image of the image intensifier and said masks comprises an optical system including adjusting means for depicting said output image on said masks with a selected magnification factor.

3. Apparatus according to claim 1, wherein said converter means comprise an optical system including adjusting means for depicting an image derived from the radiation image to be decoded on the input screen of said image intensifier with a selected magnification factor.

4. Apparatus according to claim 1, further comprising electronic, adjustable control means associated with the image intensifier and serving to depict the image formed on the input screen with a selected magnification factor.

5. Apparatus according to claim 4, wherein said adjustable control means are coupled with program control means.

6. Apparatus according to claim 1, wherein said radiation sources are arranged in a one-dimensional, quasi-random distribution pattern.

7. Apparatus according to claim 6, further comprising electronic control means associated with the image intensifier and serving to cause the output image of the image intensifier to perform a translatory movement over a selected distance.

8. Apparatus according to claim 1, characterized by a single, movably supported source of radiation; transport means for moving said radiation source in a one-dimensional track; and switching means for switching said source on and off during its movement according to a function corresponding to a quasi-random distribution pattern of a plurality of radiation sources.

* * * * *